United States Patent [19]

Khoobiar

[11] Patent Number: 4,532,365
[45] Date of Patent: * Jul. 30, 1985

[54] CONVERSION OF ALKANES TO UNSATURATED ALDEHYDES

[75] Inventor: Sargis Khoobiar, Kinnelon, N.J.

[73] Assignee: The Halcon SD Group, Inc., New York, N.Y.

[*] Notice: The portion of the term of this patent subsequent to Oct. 23, 2001 has been disclaimed.

[21] Appl. No.: 468,524

[22] Filed: Feb. 22, 1983

Related U.S. Application Data

[63] Continuation-in-part of Ser. No. 420,077, Sep. 20, 1982, , and a continuation-in-part of Ser. No. 368,196, Apr. 14, 1982, Pat. No. 4,413,147.

[51] Int. Cl.³ .............................................. C07C 45/34
[52] U.S. Cl. .................................... 568/479; 568/476; 585/629
[58] Field of Search ................. 568/476, 479; 585/629

[56] References Cited

U.S. PATENT DOCUMENTS

| | | | |
|---|---|---|---|
| 3,161,670 | 12/1964 | Adams et al. | 568/479 |
| 3,470,239 | 9/1969 | Russell | 568/479 |
| 3,479,416 | 5/1967 | Tschopp et al. | |
| 3,492,248 | 1/1970 | Notari et al. | 585/629 |
| 3,692,701 | 9/1972 | Box, Jr. | 252/166 |
| 3,784,483 | 1/1974 | Cichowald | 252/437 |
| 3,954,855 | 5/1976 | Wada et al. | 568/479 |
| 4,005,985 | 2/1977 | Hutson, Jr. | 23/288 |
| 4,041,099 | 9/1977 | Hutson, Jr. | 585/629 |
| 4,070,413 | 1/1978 | Tamotsu | 585/629 |
| 4,083,883 | 4/1978 | Hayes | 585/629 |
| 4,144,277 | 3/1979 | Walker et al. | 585/629 |
| 4,176,140 | 11/1979 | Bertus et al. | 585/629 |
| 4,260,822 | 4/1981 | Krieger et al. | 568/479 |
| 4,267,386 | 5/1981 | Vanderspurt | 568/479 |
| 4,306,090 | 12/1981 | Kirch et al. | 568/479 |

FOREIGN PATENT DOCUMENTS

| | | | |
|---|---|---|---|
| 0000663 | 10/1981 | European Pat. Off. | 568/479 |
| 0042252 | 12/1981 | European Pat. Off. | 585/629 |
| 1340891 | 12/1973 | United Kingdom | 568/479 |
| 2030885 | 9/1979 | United Kingdom | 568/479 |

Primary Examiner—Werren B. Lone
Attorney, Agent, or Firm—William C. Long; Riggs T. Stewart; Harold N. Wells

[57] ABSTRACT

Alkanes, particularly propane and isobutane are converted to unsaturated aldehydes, particularly acrolein and methacrolein in an integrated two-step process wherein the alkane is dehydrogenated in a first step to the corresponding olefin, hydrogen, and by-products and the reaction effluent is passed directly into a second step where the olefin is oxidized to the corresponding unsaturated aldehyde without significant oxidation of the hydrogen and by-products. The aldehydes and by-products may be separated and the unreacted olefin and alkane recycled to the first step. Alternatively, the effluent from the second step may be used as feed to a further oxidation step for conversion of the unsaturated aldehyde to the corresponding unsaturated acid.

4 Claims, 4 Drawing Figures

CONVERSION OF ALKANES TO UNSATURATED ALDEHYDES

CROSS-REFERENCE TO RELATED APPLICATIONS

This application is a continuation-in-part of Ser. No. 420,077, filed Sept. 20, 1982, and a continuation-in-part of Ser. No. 368,196, filed Apr. 14, 1982, now U.S. Pat. No. 9,413,147.

PRIOR ART

The invention relates generally to the preparation of unsaturated aldehydes, acids and their esters. In one aspect, the invention relates to the preparation of methacrolein, which is a precursor of methacrylic acid in a two-step process for manufacture of methacrylic acid from isobutylene or tertiary butyl alcohol. In typical processes of the prior art isobutylene or tertiary butyl alcohol is reacted in the vapor phase with molecular oxygen over a catalyst to produce methacrolein. The methacrolein is then separated and reacted with molecular oxygen in the vapor phase over a different catalyst to form methacrylic acid. The methacrylic acid may then be reacted with a suitable alcohol to form a methacrylate ester.

In another specific aspect, the invention relates to the preparation of acrolein, or acrylic acid, from in a process similar to the one described for methacrolein or methacrylic acid.

Generally, the feed for this process has been the unsaturated olefin or its equivalent alcohol. Any saturated hydrocarbon present was considered to be essentially an inert since little, if any, oxidation occured. However, an economic incentive exists for the use of alkanes as feedstocks for the preparation of unsaturated aldehydes and acids. For example, it is known to dehydrogenate isobutane to form isobutylene for use in its many applications, such as preparing of tertiary butyl alcohol, methyl tertiary butyl ether, and butyl rubber. Such dehydrogenation processes could be used to prepare isobutylene as a feedstock for the known methods of preparing methacrolein. However, if the isobutylene were separated and purified this would be an uneconomic way of preparing methacrolein and methacrylic acid. The same comment applies to the conversion of propane to acrolein or acrylic acid.

In general, integrated processes are not generally used because the by-products of dehydrogenation must be separated, since they cannot be present in the subsequent use of the olefin, without causing contamination of the ultimate end product. The present process relates to an integrated process whereby the dehydrogenation of isobutane is combined with the oxidation of the resulting isobutylene to methacrolein in a continuous manner and without intermediate separation of the isobutylene. A corresponding process can be carried out with propane as feed and producing acrolein or acrylic acid.

Processes of background interest include one shown in U.S. Pat. No. 3,470,239 in which isobutane is the feedstock to a process for methacrylic acid or methyl methacrylate via a tertiary butyl hydroperoxide intermediate. Isobutane is oxidized to a hydroperoxide and then used to oxidize methacrolein to methacrylic acid. In that oxidation tertiary butyl alcohol is a by-product which then can be used as a feedstock to prepare methacrolein in a conventional oxidation process. Consequently, isobutane only serves indirectly as a feedstock to the preparation of methacrolein.

In British Pat. No. 1,340,891 isobutane and oxygen are reacted to prepare isobutylene and/or methacrolein over a variety of base metal oxide catalysts. Since the conversion of isobutane is quite low, high concentrations of isobutane are used so that the net amount of isobutylene or methacrolein produced is sufficient to result in an practical process. Propane is also shown to provide a parallel reaction.

A recent U.S. Pat. No. 4,260,822 discloses a process for direct oxidation of isobutane to methacrylic acid in a single step, again using large amounts of isobutane in order to overcome the relatively low conversion of isobutane to the product. Again, propane is disclosed to be oxidized to acrylic acid in the same manner.

The above one-step processes are not economic, since the conversions are quite low and require handling of substantial amounts of unreacted feed with recycling in order to produce a high overall conversion of isobutane. Also, the catalysts typically do not have the long useful life necessary for satisfactory commercial operations.

Since isobutylene has a number of uses other than the preparation of methacrylic acid, a number of processes have been developed for converting isobutane to isobutylene. In U.S. Pat. No. 3,784,483 a cobalt, iron, and phosphorus catalyst is used for the oxidative dehydrogenation of isobutane to isobutylene or propane to propylene. The process of British Pat. No. 1,340,891 is similar except that generally high ratios of isobutane to oxygen (about 4/1) are used. In U.S. Pat. No. 3,479,416, a process operating in the absence of oxygen employs a base metal catalyst, particularly one containing chromium, molybdenum, and vanadium. In a group of patents typified by U.S. Pat. No. 4,083,883 a precious metal combined with promoter metals on a support is used for the dehydrogenation of paraffins, particularly normal paraffins.

Another approach is taken in U.S. Pat. Nos. 3,692,701, 4,005,985 and 4,041,099. In these processes large quantities of steam are used to dehydrogenate butanes over a catalyst of platinum-tin on zinc aluminate with a high selectivity to the corresponding butene, or propane to propylene. Relatively high conversions are achieved. Dehydrogenation of paraffins is also shown over zinc titanate catalysts in U.S. Pat. Nos. 4,144,277 and 4,176,140.

In a recent published European patent application No. 42252, isobutylene is prepared by dehydroisomerizing n-butane over a supported catalyst containing a Group IIIA element or compound, especially gallium.

Many patents have disclosed processes for oxidation of isobutylene to methacrolein. Of particular interest with respect to the present process is that disclosed in British patent application No. 2,030,885A, in which isobutylene along with oxygen and steam is passed over a molybdenum-based catalyst, providing a high conversion and selectivity to methacrolein.

Many patents have disclosed processes for oxidation of propylene to acrylic acid, such as EP No. 0000663 and U.S. Pat. No. 3,954,855. These processes are generally carried out in two steps in order to obtain the best yields of acrylic acid. In the first step, propylene is oxidized to acrolein in the vapor-phase over a promoted molybdenum catalyst and the effluent from the reaction is passed with added oxygen over a second promoted molybdenum catalyst to produce acrylic acid.

Based on the prior art discussed above, one might assemble a multi-step process whereby an alkane was dehydrogenated with or without the presence of oxygen to produce the corresponding olefins which would then be separated and purified and fed to a second step for the oxidation of the olefin to the corresponing unsaturated aldehyde. In this way, a combined process could be operated which would convert substantially all of the alkane feed to the unsaturated aldehyde by merely combining known processes. This may not be an economic way to produce the aldehyde. As will be seen, the present invention pertains to an integrated process by which an alkane may be converted to the corresponding unsaturated aldehyde without first separating the olefin.

Dehydrogenation of an alkane produces substantial amounts of hydrogen and small amounts of lower molecular weight hydrocarbons, which in the prior art processes would be removed from the product, see for example U.S. Pat. No. 3,479,416, but which in an integrated process must be accommodated in the oxidation of the alkane to the aldehyde. The hydrogen and by-products should not have an adverse effect on the oxidation catalyst or its performance. For example, the exposure of the by-products to oxidizing conditions cannot produce contaminants which reduce the quality of the aldehyde. Also, the presence of hydrogen should not create an explosive mixture in the oxidation reactor.

The oxidation step produces carbon oxides as by-products and some lower molecular weight oxygenated compounds and at the same time introduces oxygen into the gases which is not acceptable in the upstream dehydrogenation reactor. Thus, recycling a combined effluent from the oxidation reactor to the dehydrogenation step involves particular problems unique to the integrated process of the invention. The present process is able to accommodate problems involved with the integration of the prior art process by methods to be disclosed hereinafter.

SUMMARY OF THE INVENTION

Alkanes are dehydrogenated to produce the corresponding olefins, which are then oxidized to the unsaturated aldehydes. For example, methacrolein is prepared from isobutane in an integrated process in which dehydrogenation of isobutane to isobutylene is followed immediately, i.e. without separation of isobutylene from the dehydrogenation effluent, by addition of oxygen and then oxidation of the isobutylene to methacrolein. Alternatively, some of the dehydrogenation by-products may be removed before the oxidation step, thereby concentrating the isobutylene. This may be done, for example, by selective oxidation of hydrogen to water or partial condensation of the water contained in the effluent stream. Methacrolein may be recovered by scrubbing or quenching the oxidation reaction effluent which also contains unreacted isobutane, isobutylene, and oxygen, plus hydrogen, carbon oxides and miscellaneous hydrocarbon by-products of the dehydrogenation and oxidation reactions. The corresponding process may be carried out with a propane feed.

In some embodiments of the invention methacrolein is recovered and then oxygen, hydrogen, and carbon oxides are removed from the oxidation reaction effluent by catalytic reactions or absorption techniques and the remaining gases containing unreacted isobutane and isobutylene are recycled to the dehydrogenation reaction. A preferred method of removing oxygen and hydrogen is to react them over a suitable oxidation catalyst at conditions selected to completely remove the oxygen, but having substantially no effect upon the isobutylene and isobutane present. Suitable catalysts include platinum or other Group VIII noble metals on alumina or other supports. The oxidation of hydrogen is carried out at a temperature which permits selective oxidation of the hydrogen. With platinum on alumina, such oxidations may be initiated at relatively low temperatures, such as ambient. In a preferred embodiment, the oxygen supplied to the oxidation reaction is adjusted to provide a limited amount in the effluent so that the hydrogen produced in the dehydrogenation reaction consumes all of the oxygen remaining after isobutylene has been oxidized to methacrolein.

In an alternative embodiment, the alkane and the olefin remaining in the effluent gases after the aldehyde has been removed are absorbed with a suitable liquid such as a $C_8$ to $C_{10}$ paraffin oil. The gases can be further processed if desired to recover valuable components, burned, or otherwise disposed of. In this embodiment, the hydrogen and oxygen are contained in the waste gases and only the unconverted hydrocarbons are recycled to the dehydrogenation reactor.

In still another embodiment, the effluent gases are partially separated after the dehydrogenation step, with the concentrated $C_3$ or $C_4$ hydrocarbons, i.e. propylene/propane or isobutylene/isobutane, supplied to the oxidation step.

The dehydrogenation of the alkane to the olefin is carried out by a vapor-phase reaction over a suitable catalyst, which may be platinum-tin on zinc aluminate or other noble and base metal catalysts. When the catalyst is platinum-tin on zinc aluminate the dehydrogenation will be carried out at about 400° to 700° C. and up to about 10 kg/cm² gauge pressure.

The oxidation of the alkane to the aldehyde may be carried out over suitable catalysts, such as mixed base metal oxides, especially molybdenum oxide-based catalysts, and particularly a catalyst comprising the oxides of molybdenum, bismuth, cobalt, iron, nickel, thallium, antimony, silica and one or more of the alkali metals.

DESCRIPTION OF THE PREFERRED EMBODIMENTS

Figure 1:
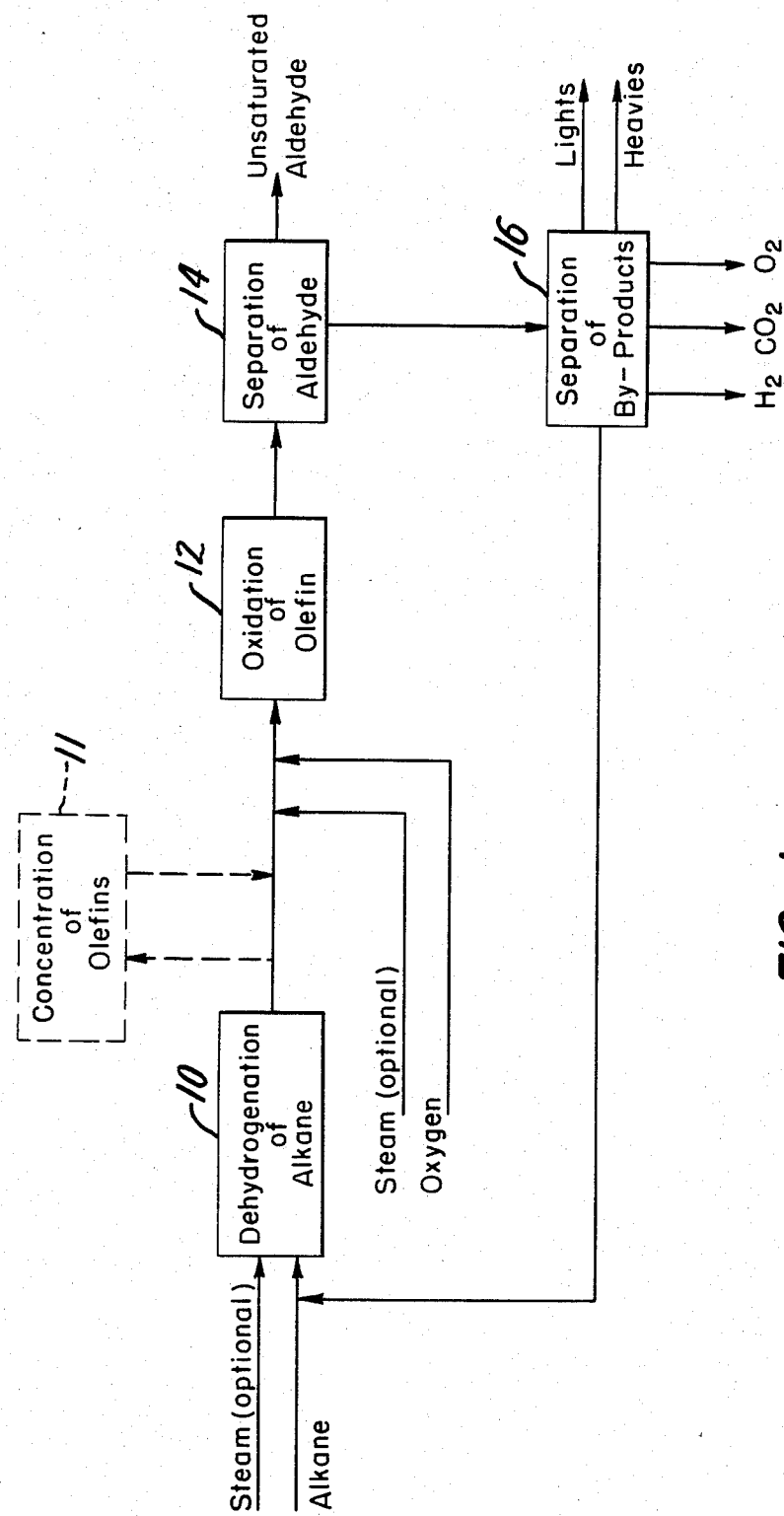
FIG. 1 is a block diagram showing the process of the invention.

In one aspect, the invention is an integrated process combining the dehydrogenation of an alkane, particularly propane or isobutane, to the corresponding olefin, i.e. propylene or isobutylene, with the subsequent oxidation of the propylene or isobutylene to acrolein or methacrolein, but without purification of the propylene or isobutylene between the two reactions. The product aldehyde is separated for further use and after separation of by-products the unreacted olefin and alkane may be recycled to the dehydrogenation step if desired. A schematic view of such a complete process is shown in FIG. 1.

Although discussed specifically as it relates to isobutane, it should be understood that the process may be applied also propane.

The process contrasts with those of the prior art in that the two reactions are operated so that the effluent from the dehydrogenation reaction 10 may be fed directly to the oxidation reaction 12 for conversion of isobutylene to methacrolein. One familiar with the prior art would expect that isobutylene would be separated from the effluent of the dehydrogenation step before feeding it to the oxidation step. Since the dehydrogenation of isobutane involves the production of significant quantities of hydrogen, as well as small amounts of lower molecular weight hydrocarbons, the isobutylene must be oxidized in the presence of significance quantities of hydrogen and by-products, without significantly affecting the oxidation of isobutylene to methacrolein or causing oxidation of the hydrogen. I have found that isobutylene may be oxidized to methacrolein in the presence of hydrogen and by-products of the dehydrogenation step, while not adversely affecting the oxidation process.

In an alternative embodiment, a partial separation (11) may be made by absorption or distillation techniques familiar to those skilled in the art to provide a concentrated $C_4$ hydrocarbon feed to the oxidation step (12). Depending upon the dehydrogenation effluent composition, it may be desirable to remove any or all of the following: hydrogen, light hydrocarbons, and water, in whole or in part. The benefits of the invention are still retained at least in part, since an impure feed is supped to the oxidation step. Most conveniently this concentration may be accomplished by oxidizing the hydrogen to water and/or condensing a portion of the water contained in the effluent from dehydrogenation.

In one aspect of the invention, after methacrolein is separated (14) from the oxidation reactor effluent a gas containing unreacted isobutylene and isobutane is returned to the dehydrogenation step. Since excess oxygen is employed to oxidize isobutylene to methacrolein, this recycle stream contains substantial quantities of oxygen which may not enter the dehydrogenation step. Any oxygen present would be reacted at the operating temperature causing a loss of the $C_4$ components. Processes which employ oxygen in dehydrogenation characteristically use only minor amounts relative to the isobutane. Thus, in order to assemble a complete process wherein isobutane is converted only to methacrolein (plus minor amounts of by-products), it is necessary to remove (16) both the hydrogen formed during the dehydrogenation step and excess oxygen remaining after the oxidation step plus carbon dioxides and other by-products. The allowable level of each component in the gas will be adjusted as necessary. In a preferred embodiment, carbon dioxide is scrubbed out and by-products are purged, after which hydrogen is oxidized to water over an oxidation catalyst under conditions such that substantially no loss of the $C_4$ components occurs. In another embodiment, the isobutane and isobutylene are scrubbed from the effluent gases and recovered for recycle to the dehydrogenation step while the gases are discarded.

The dehydrogenation of isobutane produces one mol of hydrogen for each mol of isobutylene and additional hydrogen from the formation of lower molecular weight by-products. If isobutylene is not separated before subsequent oxidation, as in this process, the hydrogen and other by-products are carried into the subsequent oxidation reaction. Oxidation of the by-products to compounds which contaminate methacrolein must be avoided. Oxidizing the hydrogen along with isobutylene would be undesirable since it would consume oxygen and interfere with the oxidation of isobutylene. Also, oxidation of hydrogen would generate undesirable heat and could create hot-spots in the reactor tubes and lower the productivity for methacrolein. However, it has been found that oxidation of isobutylene can be carried out in the presence of hydrogen with substantially no consumption of hydrogen, as will be seen in the following example.

EXAMPLE 1

Oxidation of Isobutane in the Presence of Hydrogen

A feed gas simulating the effluent expected to result from the dehydrogenation of isobutane in the presence of steam was blended and fed to an oxidation reactor for production of methacrolein. The gas composition was 7 vol % tertiary butyl alcohol, 15 vol % steam, 15 vol % oxygen, 3.2 vol % hydrogen and the balance nitrogen. Note that tertiary butyl alcohol dehydrates to form isobutylene, for which it is generally considered to be an equivalent in the oxidation reaction. The gas was passed at a gas hourly space velocity (GHSV) of 2300 $hr^{-1}$ and a pressure of about 1.6 kg/cm$^2$ gauge over 160 cc of a catalyst having a size of ⅛″ diameter and disposed in a 0.5″ i.d. tubular reactor. The heat of reaction was removed and the temperature adjusted by a circulating molten salt in the usual manner of carrying out such reactions. The oxidation catalyst had the nominal formula

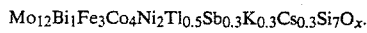

$Mo_{12}Bi_1Fe_3Co_4Ni_2Tl_{0.5}Sb_{0.3}K_{0.3}Cs_{0.3}Si_7O_x$.

The results of two tests are compared in the table below; test 1 shows the results with hydrogen present and test 2 shows the results after the hydrogen supply was cut off.

TABLE A

| Test No. | Reactor Temp. °C. | Conversion of TBA % | % Selectivity to | | | |
|---|---|---|---|---|---|---|
| | | | MCHO[1] | MAA[2] | HOAC[3] | $CO_x$[4] |
| 1 | 346 | 85.2 | 83.4 | 3.9 | 2.5 | 8.9 |
| 2 | 346 | 86.7 | 82.1 | 2.9 | 2. | 10.3 |

[1]MCHO - methacrolein
[2]MAA - methacrylic acid
[3]HOAC - acetic acid
[4]$CO_x$ - carbon oxides The tests show differences not considered significant, but within the normal variation of the test measurements. The amount of hydrogen consumed was not accurately measured because of the small quantities involved, but it was clear from analysis of the reactor effluent that little of the hydrogen must have been oxidized. However, the data show that it had little or no effect in the oxidation of isobutylene to methacrolein.

Additions of small amounts of other $C_4$ by-products of the dehydrogenation reaction, such as n-butenes also appear to have little or no effect on the oxidation to methacrolein.

Separation of methacrolein (14) may be done by methods known to the prior art. See for example, U.S.

Pat. No. 4,234,519. This may be done by cooling and condensing water-containing methacrolein from the isobutylene reactor effluent followed by scrubbing of the resulting gas with a recirculating water stream in order to complete the removal of methacrolein. The resulting methacrolein solutions may be stripped at a convenient time to produce a methacrolein-containing vapor for subsequent use. Other alternatives, such as solvent extraction and the like may be used.

Although separation of methacrolein for subsequent oxidation to methacrylic acid (or other use) is shown, it is possible, provided that the catalyst is resistant to the various compounds present, to feed the effluent of the oxidation step 12 directly to another oxidation step for conversion of methacrolein to methacrylic acid. It would be preferred to operate oxidation step 12 to convert substantially all of the isobutylene to methacrolein before carrying out the oxidation to methacrylic acid.

In its broad form, the invention includes the combination of dehydrogenation and oxidation steps whereby isobutane is converted to methacrolein. Such a combination process without an intermediate separation of isobutylene has been shown to be possible. If the resulting by-product stream containing significant quantities of isobutylene and isobutane can be used for other purposes, then recycling of the gas is not required. In many cases, it will be desirable to recycle unreacted isobutylene and isobutane so that the integrated process substantially converts isobutane to methacrolein with only minor amounts of by-products and without ever producing a substantially pure isobutylene stream. In order to recycle gas containing large amounts of isobutane and isobutylene, it will be necessary to remove hydrogen produced in the dehydrogenation step, excess oxygen from the oxidation step, and carbon oxides formed in both steps. In addition, a purge of light and heavy by-products and feed impurities will be taken. Removal of carbon dioxide typically would be done by scrubbing all or a portion of the recycle stream with a carbonate or amine solution known in the art in order to maintain the desired level of carbon dioxide. Carbon monoxide will be converted to carbon dioxide in the dehydrogenation reactor. Since the presence of these materials is not critical to either the dehydrogenation or oxidation steps, they may be economically permitted to build up in the recycle stream to a level in which they may be conveniently and economically removed. Since the light and heavy hydrocarbon by-products, such as methane, ethane, ethylene, propane, propylene, pentane, and pentene boil at temperatures significantly different from those of methacrolein or the $C_4$ hydrocarbons, they may be separated by distillation or purging of streams containing the by-products in concentrated amounts. Removal of the hydrogen formed by the dehydrogenation of isobutane might be done by various methods such as catalytic oxidation, liquid phase absorption or gas phase adsorption. In a preferred embodiment of the invention, both the hydrogen and oxygen are disposed of at the same time by reacting them to form water in a vapor phase over a suitable oxidation catalyst under conditions such that substantially all of the hydrogen and oxygen present are removed. This can be accomplished without significant loss of the $C_4$ components as will be seen.

Hydrogen, as a by-product of the dehydrogenation of isobutane, must be disposed of if unreacted isobutane is to be recycled. As previously seen, the oxidation of isobutylene is carried out in such a manner that little, if any, hydrogen is consumed. According to a preferred embodiment of the invention, the amount of oxygen in the feed to the oxidation of isobutylene is adjusted so that the effluent contains no more oxygen than can react with the hydrogen present. Obviously, neither oxygen or hydrogen should be present in significant quantities in the dehydrogenation reactor, which should operate with only isobutane and steam as feeds for maximum yield. Removal of oxygen is more important, but hydrogen could be permitted in minor amounts. It has been found that such selective oxidation of hydrogen can be carried out without loss of the valuable isobutane or isobutylene, as will be seen in the following example.

EXAMPLE 2

Selective Oxidation of Hydrogen

A feed gas simulating the recycle gas after the methacrolein has been removed as product was fed to an 0.5" i.d. oxidation reactor containing 75 cc of ⅛" alumina pellets having a surface area of about 150 m²/gm and impregnated with 0.3 wt % platinum. The gas was fed at a GHSV of 2000 hr$^{-1}$ and about atmospheric pressure. Its composition was 30 vol % isobutane, 4 vol % hydrogen, 3 vol % oxygen, and 63 vol % nitrogen. The reaction was carried out at essentially ambient temperature, where it is found that all of the hydrogen is consumed, but substantially none of the isobutane.

While it is preferred to carry out the selective oxidation of hydrogen in the recycle gas, it is feasible to introduce the equivalent step after the dehydrogenation of isobutane and before the oxidation of isobutylene. Although a concentration of the isobutylene would be achieved, alternative means must be provided to prevent excess oxygen from returning to the dehydrogenation step.

EXAMPLE 3

Dehydrogenation of Propane

A catalyst composed of 0.4 wt % Pt and 1 wt % In impregnated on a zinc aluminate support was prepared. A catalyst sample of 50 cc as 3 mm extrudate was charged to a tubular reactor having 25.4 mm i.d. An additional 250 cc of the zinc aluminate support was added to the reactor above the catalyst bed. A gas stream containing 1 mol of propane for each 2 mols of steam was fed to the reactor at a gas hourly space velocity of 4000 hr$^{-1}$ under a pressure of 3.5 kg/cm² gauge. The inlet to the catalyst bed was held at a predetermined temperature, with the outlet temperature reflecting the endothermic nature of the dehydrogenation reaction. The results are given below in Table B.

TABLE B

| Test | Inlet Temp. °C. | Conversion of Propane, % | Selectivity to Propylene, % |
|---|---|---|---|
| 1 | 548 | 23.6 | 95.8 |
| 2 | 523 | 29.7 | 96.5 |

The dehydrogenation of propane produces one mol of hydrogen for each mol of propylene and additional hydrogen from the formation of some lower molecular weight by-products. If propylene is not separated before subsequent oxidation, as in this process, the hydrogen and other by-products are carried into the subsequent oxidation reaction. Oxidation of the by-products to compounds which contaminate acrolein must be avoided. Oxidizing the hydrogen along with propylene would be undesirable since it would consume oxygen and interfere with the oxidation of propylene. Also, oxidation of hydrogen would generate undesirable heat and could create hot-spots in the catalyst and lower the productivity for acrolein. However, it has been found that oxidation of propylene can be carried out in the presence of hydrogen with substantially no consumption of hydrogen, as will be seen in the following example. The presence of propane which has not been dehydrogenated also appears to have no significant effect on the oxidation of propylene.

EXAMPLE 4

Oxidation of Propylene in the Presence of Hydrogen and Propane

A catalyst was prepared according to the method described in EP No. 0000663 corresponding to Reference Catalyst A and having a composition of 80% (wt.) $K_{0.1}Ni_{2.5}Co_{4.5}Fe_3Bi_1P_{0.5}Mo_{12}O_x$ and 20% $SiO_2$. A charge of 220 cc of catalyst as 4.7 mm pellets was placed in a single-tube reactor having an i.d. of 12.7 mm. A feed gas containing 5 vol % propylene, 20 vol % steam and 12% oxygen was passed at a volume hourly space velocity of 1200 $hr^{-1}$ over the catalyst. The pressure in the catalyst was about 1.76 $kg/cm^2$ gauge. Analysis by gas chromatography of the effluent gases gave the results designated in test 3-6 Table C.

TABLE C

| Test No. | Time, hrs. | Temp. °C. | Conversion of Propylene, % | Selectivity to Acrolein and Acrylic Acid, % |
| --- | --- | --- | --- | --- |
| 3 | 78.0 | 310 | 91.1 | 87.4 |
| 4 | 81.0 | 310 | 90.6 | 86.3 |
| 5 | 93.5 | 310 | 90.5 | 87.7 |
| 6 | 99.5 | 310 | 90.1 | 89.7 |
| 7 | 102 | 310 | 94.2 | 86.6 |
| 8 | 115 | 309 | 92.6 | 88.7 |
| 9 | 124 | 309 | 92.5 | 87.9 |
| 10 | 139 | 309 | 89.3 | 87.2 |
| 11 | 147 | 309 | 91.4 | 85.6 |
| 12 | 156 | 310 | 93.7 | 86.7 |
| 13 | 180 | 309 | 92.9 | 86.9 |

After the performance of the catalyst had been established with only propylene feed, hydrogen was added to the feed gas to simulate in part the conditions which would pertain to the oxidation reaction when supplied with propylene produced by dehydrogenation of propane. An additional 4 vol % of hydrogen was included with the mixture previously fed. The results are shown as tests 7-10 in Table C. It will be seen that substantially the same results were achieved as in tests 3-6. It was concluded that essentially no hydrogen was being oxidized, judging from the operating conditions in the reactor.

The hydrogen was discontinued and the oxidation reaction continued with 4 vol % propane added. The results are shown as tests 11-13 in Table C. Again substantially the same results were obtained as in tests 3-6, indicating that propane was not affecting the oxidation of propylene and was not itself being oxidized.

These results show that propylene can be oxidized in the presence of hydrogen and propane, the two principal components of the dehydrogenation of propane to propylene. It may be concluded that the integration of the dehydrogenation and oxidation reactions is feasible.

EXAMPLE 5

Oxidation of Acrolein in the Presence of Hydrogen Propane

To illustrate the oxidation of acrolein to acrylic acid and the effect of hydrogen and propane additions to the feed gas, experiments were carried out which parallel those of Example 1.

A catalyst was prepared corresponding to the composition of Example 1 of U.S. Pat. No. 3,954,855 and according to the procedure described there. The catalyst composition was $Mo_{12}V_{4.8}Sr_{0.5}W_{2.4}Cu_{2.2}O_x$. A 73 cc sample of the catalyst as 4.7 mm pellets was placed in a tubular reactor having 12.7 mm i.d. The reactor was surrounded by a bath thermostatically providing a uniform predetermined temperature. The feed to the reactor was initially 6-8 vol % acrolein, 51 vol % air, and 45 vol % steam. The volumetric space velocity was 3000 $hr^{-1}$ and the average reactor pressure slightly above atmospheric. The results are shown in Table D.

TABLE D

| Test No. | Time, hrs. | Temp. °C. | Conversion of Acrolein, % | Selectivity to Acrylic Acid, % |
| --- | --- | --- | --- | --- |
| 14 | 126 | 254 | 92.8 | 89.1 |
| 15 | 126 | 251 | 84.5 | 89.2 |
| 16 | 41 | 252 | 86.8 | 88.4 |
| 17 | 36 | 251 | 80.7 | 87 |

As was done in Example 4, first 4 vol % hydrogen was added and then the hydrogen was replaced with propane. The results are shown in Table D as Test 16 ($H_2$) and 17 (propane). Although some difference in the conversion of acrolein appears, it is clear from Test 14 and 15 that conversion is very sensitive to temperature and the differences among Tests 15, 16, and 17 are not considered significant. The selectivity to acrylic acid is substantially the same.

Figure 2:
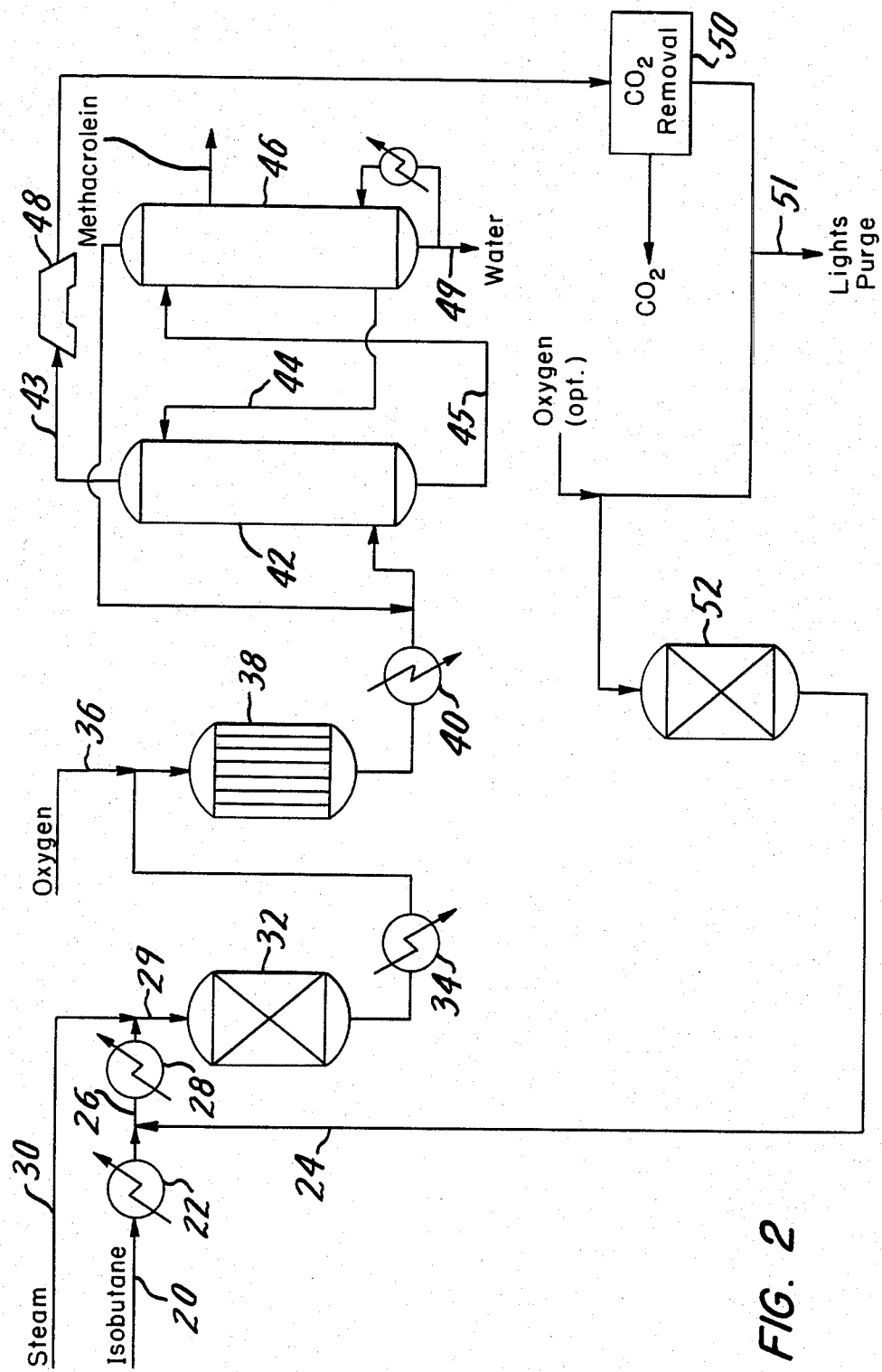
FIG. 2 is a simplified flowsheet showing production of methacrolein from isobutane according to one embodiment of the invention.

FIG. 2 is a simplified flowsheet showing a preferred embodiment of the invention with a complete process whereby isobutane is converted substantially to methacrolein. Fresh isobutane feed 20 is vaporized in exchanger 22 and combined with recycle stream 24 containing substantial amounts of isobutane and isobutylene. The combined stream 26 is then heated in exchanger 28 to a temperature such that when combined with the required amount of steam (30) the temperature obtained will be that suited for the dehydrogenation of isobutane to isobutylene. The amount of steam used must also be suitable for the subsequent oxidation of the isobutylene to methacrolein. As shown here, steam is supplied as a fresh feed stream. If this is done, then water produced in the reactions is eventually purged from the system from the bottom of the methacrolein stripper 46. Since the process is a net producer of water, this water may be used to provide the steam for the process. In either case, a feed stream containing isobutane and steam in molar ratios between 1/1 and 1/10, preferably ½ to 1/5, is fed at temperatures between about 400°-700° C. preferably about 650° C. and at pressures between about 2-10 $kg/cm^2$ gauge, preferably about 3 $kg/cm^2$ gauge to reactor 32 where conversion of about 40-50% of the isobutane is converted to isobutylene with a selectivity of 90% or more.

A number of catalysts have been disclosed in the prior art for use in this process and the conditions under which the reaction is carried out will depend on the catalyst selected. Of particular usefulness is a platinumbased catalyst of the type shown in U.S. Pat. No. 4,005,985 specifically for this process. Although platinum and tin disposed on a zinc aluminate support provides good performance, other catalysts which have been found effective include platinum and rhenium or indium supported on zinc aluminate. Other Group VIII noble metals, alone or in combination on various supports known to the art may have application in the dehydrogenation of isobutane to isobutylene.

Other potential supports would include alumina, other alkaline earth metal aluminates, and rare earth aluminates including lanthanum. Promoters such as tin, lead, antimony, and thallium may be used. Base metal catalysts such as the chromium, zirconium, titanium, magnesium and vanadium oxides as shown in U.S. Pat. Nos. 3,479,416 and 3,784,483 or the zinc titanate of U.S. Pat. Nos. 4,176,140 and 4,144,277 also might be used. The invention is not considered to be limited to specific catalyst formulations.

It will be understood by those skilled in the art that this type of process involves a rapid deactivation of the catalyst and typically the process will be operated with multiple reactors so that frequent regeneration is possible. The details of such operations are, however, not considered part of the invention. The dehydrogenation reaction is endothermic and the temperature leaving the reactor 32 will be on the order of 100°–200° C. lower than the inlet temperature. This will be affected by the amount of steam employed, the condition of the catalyst, and the severity of the reaction conditions chosen.

The dehydrogenation reactor effluent is cooled in exchanger 34 to a suitable temperature for inlet to the oxidation reactor 38 and joined with an oxygen stream 36 to provide a suitable feed for the oxidation of isobutylene to methacrolein. Substantially pure oxygen is preferred, although less pure oxygen could be used if means were provided for purge of the additional inert gases that would normally be present. The reaction would be carried out under conditions typical of the art, that is, temperatures in the range of about 300°–400° C., pressures of about 1-8 kg/cm$^2$ gauge, and gas hourly space velocities on the order of 2000-3000 hrs$^{-1}$. A suitable oxidation catalyst will be used, typically a mixture of base metal oxides, especially those which are molybdenum-based, particularly a catalyst comprising the elements molybdenum, bismith, cobalt, iron, nickel, thallium, antimony, and one or more of the alkali metals. The reactor typically will be of the tubular type where the pelleted catalyst is placed inside tubes which are surrounded by a heat transfer fluid for the removal of the heat of reaction. Typically 60-95% of the isobutylene feed to the reactor will be converted to methacrolein, along with minor amounts of methacrylic acid, acetic acid, and less significant quantities of lighter and heavier by-products. A certain amount of the isobutylene is burned to carbon oxides and water. If the reactor is operated to oxidize substantially all of the isobutylene then it may be possible to feed the reactor effluent directly to a second oxidation step for the further oxidation of methacrolein to methacrylic acid.

The resulting gaseous mixture may be cooled and fed to an absorber tower 42 where methacrolein is absorbed in a recirculating water stream 44 at temperatures in the range of about 15°–20° C. Substantially all of the methacrolein is recovered in a solution containing up to about 2 mol % methacrolein. This solution may be stored for further use or may be immediately sent to a methacrolein stripper 46 where, at lower pressure and with the application of heat, methacrolein is stripped from the water and withdrawn as the vapor side stream. The stripped water is returned (44) to the top of the methacrolein absorber 42 for further use. Water produced in the process is removed (49) for disposal or recirculation as steam in the dehydrogenation step. The light gases leaving the top of the methacrolein absorber 42 contain large quantities of isobutylene and isobutane along with lesser amounts of carbon oxides, hydrogen, oxygen, and light impurities. These gases are compressed (48) if they are to be returned as a recycle stream for further conversion of the C$_4$'s to methacrolein. All or part of the stream may be scrubbed for removal of carbon dioxide as is shown only schematically (50), since it represents a technique familiar to those skilled in the art. For example, amine or hot carbonate scrubbing may be employed. In order to prevent build up of light impurities such as methane, ethane, ethylene, propane and propylene, a purge stream 51 may be taken continuously or intermittently from the recycle stream as shown.

The gas still contains significant quantities of hydrogen made in the dehydrogenation of isobutane and excess oxygen supplied to the oxidation reactor. Both of these must be removed. It is a feature of one embodiment of the invention to adjust the amount of oxygen supplied to the reactor 38 so that no more remains in the effluent than can be reacted with the hydrogen produced in the dehydrogenation reaction. Such an oxidation is shown being carried out in oxidation reactor 52 employing a catalyst capable of oxidizing hydrogen to water at relatively low temperatures so that the C$_4$ components are substantially unaffected, as has been shown in Example 2 above. Various oxidizing catalysts may be used for this purpose, such as noble metals or base metals. In particular, platinum or palladium on alumina has been found particularly useful since the reaction can be initiated at near ambient temperature. However, any convenient temperature up to about 400° C. might be employed. Alternately, platinum on a zeolite support sized to exclude C$_4$ hydrocarbons could be chosen. Such catalysts are capable of completely oxidizing hydrogen to water without oxidizing C$_4$ components. Thus, the recycle stream is passed over the selective oxidation catalyst (52) for removal of both hydrogen and oxygen and, thereafter, passed to the dehydrogenation reactor 32 for further processing.

A typical example of the practical operation of the flow sheet shown in FIG. 2 is as follows:

EXAMPLE 6

One hundred mols/hr of a feed stream containing 95% isobutane, 3% n-butane, 1.5% pentanes, and 0.5% propane is vaporized and fed to the dehydrogenation reactor, along with 378.3 mols/hr of a recycle gas stream containing 24.9% isobutane and 19.6% isobutylene, 27% water, and essentially no oxygen or hydrogen. The combined streams 26 are heated to about 750° C. (28) and mixed with 323 mol/hr of steam (30) which may be provided by recycling and vaporizing stream 49 from the methacrolein stripper 46. The combined stream is fed to the dehydrogenation reactor 32 at about 650° C., where about 45% of the isobutane fed is converted to isobutylene. Leaving the reactor at about 520° C., the effluent stream is cooled to about 130° C. in exchanger 34 and mixed with 171 mol/hr of oxygen (36) before being supplied to the oxidation reactor 38, where about 82% of the isobutylene is converted to methacrolein. Leaving the reactor 38 at about 342° C. and 1.4 kg/cm² gauge the effluent gases are cooled to about 150° C. and passed to the absorber 42 where the methacrolein is recovered by a recirculating water stream sufficient to produce an aqueous solution containing about 1-2 mol % methacrolein. This solution is then stripped in a reboiled stripper 46 to produce a vapor sidestream product containing 69.7 mol/hr methacrolein, 6 mol/hr methacrylic acid and 9.4 mol/hr various by-products, such as acetone, acrolein, and water. The crude recycle gas leaving the top of the absorber 42 is compressed sufficiently to permit the gas to rejoin the fresh feed to the dehydrogenation reactor 32 (about 3.9 kg/cm² gauge). The 429 mol/hr vapor contains about 23.8% hydrogen, 11.9% oxygen, 21.9% isobutane, and 17.2% isobutylene. The gas also contains carbon oxides, which are allowed to accumulate to a desired level and then maintained at that level by scrubbing out the net make of carbon dioxide on each pass (50). The gas is passed through the selective oxidation reactor 52 where substantially all of the hydrogen and the oxygen are combined to produce water. The reactor is fed with the gas at about 25° C. and the effluent leaves at about 175° C. owing to the heat of combustion. The gas is returned (24) to the freshly vaporized isobutane feed (20) to complete the cycle.

Figure 3:
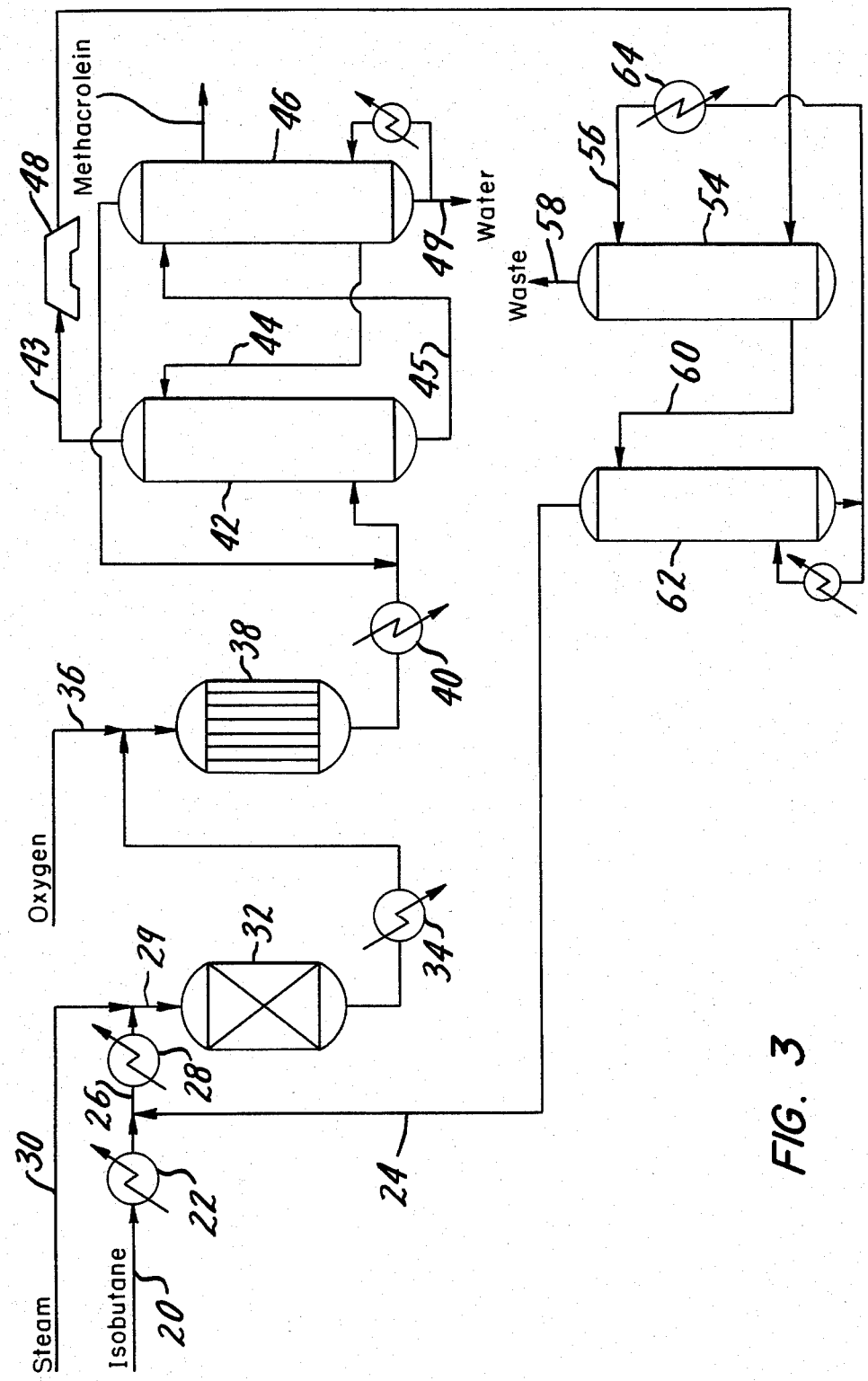
FIG. 3 is a simplified flowsheet showing production of methacrolein from isobutane according to a second embodiment of the invention.

An alternative embodiment is illustrated in FIG. 3. The dehydrogenation of isobutane to isobutylene in reactor 32, followed by the oxidation of isobutylene to methacrolein in reactor 38 and the subsequent recovery of methacrolein are the same as on the flow sheet of FIG. 2. In this embodiment, all gases are purged and only unreacted isobutane and isobutylene are recycled for further production of methacrolein. This may be accomplished by absorbing the $C_4$ hydrocarbons by suitable liquid solvents such as paraffin or aromatic hydrocarbons, or solid materials such as molecular sieves. The method of FIG. 3 employs a liquid solvent selected to efficiently separate and recover isobutane and isobutylene from the other gaseous components. One economical solvent is a paraffin oil containing $C_8$-$C_{10}$ hydrocarbons. The recycle gas containing carbon oxides, hydrogen, oxygen, and light hydrocarbon by-products is passed into an absorber tower 54 where the isobutane, isobutylene, and heavier materials are absorbed by a liquid stream 56, leaving in the vapor phase the light gases, which are withdrawn (58) from the top of the column for recovery of useful components or disposal. The $C_4$-rich liquid is withdrawn from the bottom of the column 54 and passed (60) to stripping column 62 where the $C_4$'s are stripped out. The $C_4$-lean liquid is withdrawn from the bottom of the column 62, cooled in exchanger 64 and returned (56) to the absorber 54 for reuse. The vaporized isobutane and isobutylene are recycled (24) to the dehydrogenation reactor 32. A slipstream may be taken from the $C_4$-lean solvent and distilled to separate high-boiling materials in a conventional manner (not shown).

A typical example of the practical operation of the flow sheet shown in FIG. 3 is as follows:

EXAMPLE 7

One hundred mols/hr of a feed stream containing 95% isobutane is vaporized and fed (26) to the dehydrogenation reactor 32, along with 146 mols/hr of a recycle gas stream (24) containing 62% isobutane and 38% isobutylene. The combined streams are heated and mixed with 461 mol/hr of steam (30) either as fresh steam or recycled from the methacrolein stripper 46 and vaporized. The combined stream 29 is fed to the dehydrogenation reactor 32 at about 650° C., where about 45% of the isobutane fed is converted to isobutylene. Leaving the reactor at about 520° C., the effluent stream is cooled to about 130° C. in exchanger 34 and mixed with 141 mol/hr of oxygen (36) before being supplied to the oxidation reactor 38, where about 82% of the isobutylene is converted to methacrolein. Leaving the reactor 38 at about 342° C. and 1.4 kg/cm² gauge the effluent gases are cooled to about 150° C. in exchanger 40 and passed to the absorber 42 where the methacrolein is recovered by a recirculating water stream (44) sufficient to produce an aqueous solution containing about 1-2 mol % methacrolein (45). This solution is then stripped in a reboiled stripper 46 to produce a vapor sidestream product containing 69.7 mol/hr methacrolein, 6 mol/hr methacrylic acid and various by-products including acetic acid, acrolein, and acetone. The crude recycle gas (43) leaving the top of the absorber 42 is compressed (48) sufficiently to permit the gas to rejoin the fresh feed to the dehydrogenation reactor 32 (about 3.9 kg/cm² gauge). The 302 mol/hr vapor contains about 28% hydrogen, 7% oxygen, 30% isobutane, 19% isobutylene, and 11% carbon oxides. The gas is passed through the absorber tower 54 where substantially all of the isobutane and isobutylene are scrubbed out by stream 56 containing 150 mol/hr of $C_8$-$C_{10}$ solvent. The $C_4$-rich liquid (60) passes to the stripping column 62 where the $C_4$'s are stripped and are returned (24) to the dehydrogenation reactor 32 to complete the cycle.

As with the selective oxidation step previously discussed, the absorption of $C_4$'s by a solvent could be adapted to provide a partial separation of the effluent from the dehydrogenation step so that only isobutylene and unconverted isobutane are fed to the oxidation reactor. As before, some advantages are obtained, but at additional cost and it still remains necessary to remove oxygen and carbon oxides from the gaseous effluent.

The discussion above with respect to processes by which isobutane may be converted to methacrolein also may be generally applied to an analogous process by which propane is converted to acrolein. Substantially the same technique would be employed, although one skilled in the art will understand that the operating conditions and the equipment will be modified to provide the best results, but without departing from the invention in its broader aspects.

Figure 4:
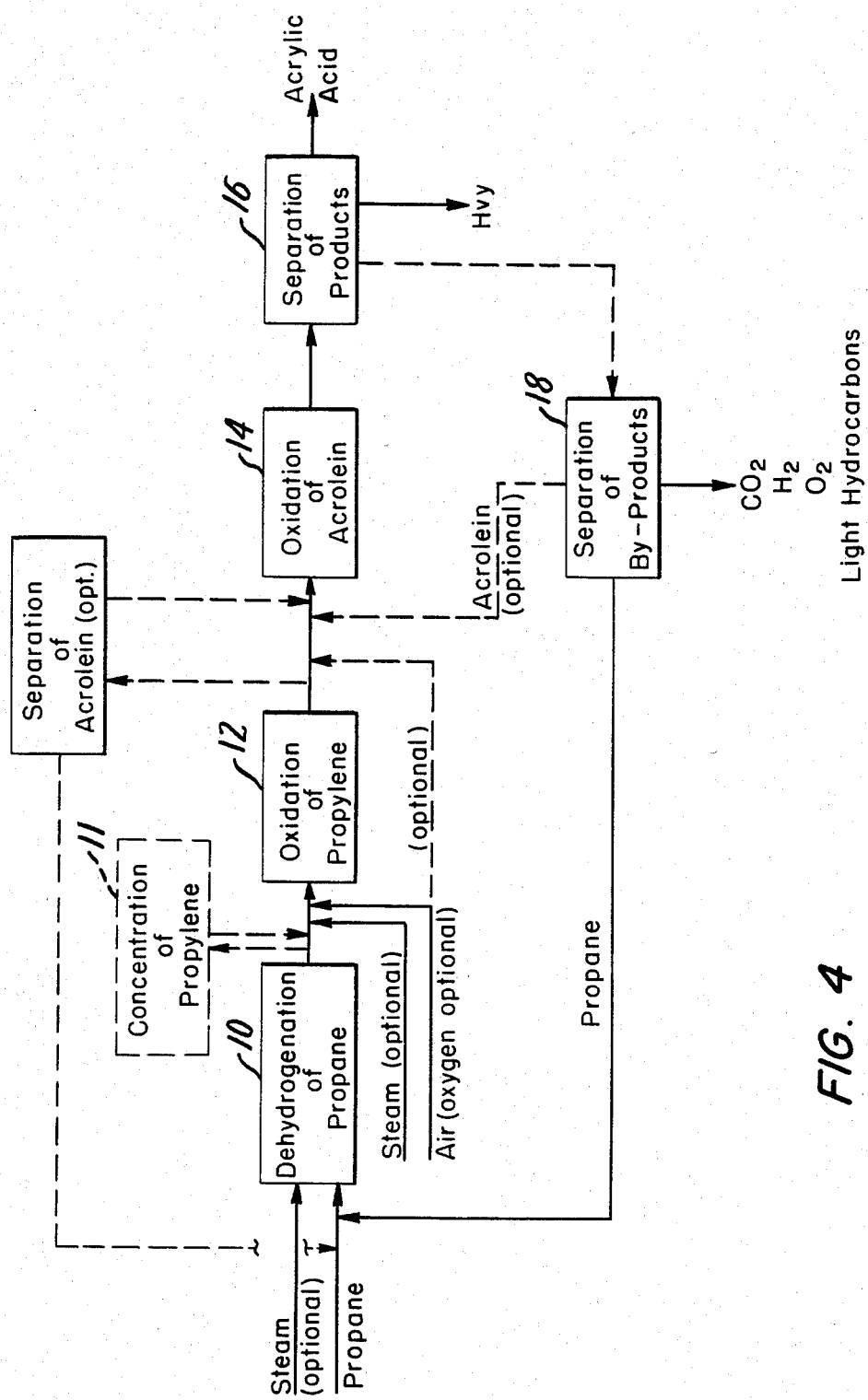
FIG. 4 is a block diagram showing the production of acrylic acid from propane according to the invention.

The usual commercially-practiced process generally produces acrylic acid, rather than acrolein. The present invention may be applied to the production of acrylic acid as shown schematically in the block diagram of FIG. 4.

The process contrasts with those of the prior art in that the effluent from the dehydrogenation reaction 10 may be fed directly to the oxidation reaction 12 for conversion of propylene to acrolein. One familiar with the prior art would expect that propylene would be separated from the effluent of the dehydrogenation step 10 before feeding it to the oxidation step 12. Since the dehydrogenation of propane involves the production of significant quantities of hydrogen, as well as small amounts of lower molecular weight hydrocarbons, the propylene must be oxidized in the presence of significance quantities of hydrogen, propane, and by-products, without significantly affecting the oxidation of propylene to acrolein or causing oxidation of the hydrogen. We have shown in the examples that propylene may be oxidized to acrolein in the presence of hydrogen, propane and by-products of the dehydrogenation step, while not adversely affecting the oxidation process.

After the propylene has been oxidized to acrolein, the entire effluent from the first oxidation step 12 may be sent directly to a second oxidation step 14 where the acrolein is oxidized to acrylic acid. Thereafter, the effluent of oxidation step 14 is partially condensed and separated at 16. Purified acrylic acid is the product while the lower-boiling components are separated at 18. Waste gases and heavy by-products are discharged while unreacted propane is recycled to steps 10 and 14.

The effluent from the first oxidation step 12 may be separated to recover acrolein, which is then fed, along with air or oxygen to the second oxidation step 14. Recovery may be made by absorption in suitable liquids, such as water and the lower carboxylic acids. Unreacted propane would be returned to the dehydrogenation step 10 as shown. If any significant amount of acrolein remains unconverted, it optionally may be separated and recycled to the oxidation stage 14 as shown.

What is claimed is:

1. A process for the preparation of unsaturated aldehyde from the corresponding alkane comprising:
   (a) dehydrogenating the alkane to the corresponding olefin in the presence of steam, over a dehydrogenation catalyst comprising a Group VIII noble metal on a support at a temperature in the range of about 400°–700° C. and up to about 10 kg/cm$^2$ gauge pressure to form an effluent stream comprising the olefin, carbon oxides, hydrogen, steam, and unreacted alkane;
   (b) mixing oxygen and optionally steam with said effluent stream of (a) and passing the mixture over a molybdenum-based oxidation catalyst at conditions selected to produce the unsaturated aldehyde and producing an effluent stream comprising the unsaturated aldehyde, unreacted alkane and olefin, oxygen, hydrogen, steam, and carbon oxides;
   (c) recovering said aldehyde from said effluent of (b);
   (d) separating from said effluent of (b) after recovery of unsaturated aldehyde therefrom the hydrogen produced in (a), the carbon oxides produced in (a) and (b), and the unreacted oxygen of (b); and
   (e) returning as feed to (a) the effluent of (b) after recovering unsaturated aldehyde, hydrogen, oxygen, and carbon oxides therefrom.

2. The process of claim 1 wherein said alkane is propane and said aldehyde is acrolein.

3. The process of claim 2 wherein said dehydrogenation step (a) is fed with propane and steam in a ratio of about 1/0.5 to 1/10.

4. A process for the preparation of acrolein from propane comprising:
   (a) dehydrogenating propane in the presence of steam, over a dehydrogenation catalyst comprising a Group VIII noble metal on a support at a temperature in the range of about 400°–700° C. and up to about 10 kg/cm$^2$ gauge pressure to form an effluent stream comprising propylene, hydrogen, carbon oxides, steam, and unreacted propane;
   (b) concentrating the propylene in said effluent of (a):
   (c) mixing oxygen with the concentrated propylene of (b) and passing the mixture over a molybdenum-based oxidation catalyst at conditions selected to produce an effluent stream comprising acrolein, unreacted propylene and propane, oxygen, hydrogen, steam, and carbon oxides;
   (d) recovering the acrolein from said effluent of (c);
   (e) separating from said effluent of (c) after recovery of acrolein therefrom the hydrogen produced in (a), the carbon oxides produced in (a) and (c), and the unreacted oxygen of (c); and
   (f) returning as feed to (a) the effluent of (c) after recovering acrolein, hydrogen, oxygen, and carbon oxides therefrom.

* * * * *